United States Patent [19]

Hill

[11] 4,100,132

[45] Jul. 11, 1978

[54] STABILIZED POLYOLEFIN COMPOSITION

[75] Inventor: Harry Elwyn Hill, Wallingford, Conn.

[73] Assignee: R. T. Vanderbilt Company, Inc., Norwalk, Conn.

[21] Appl. No.: 668,842

[22] Filed: Mar. 22, 1976

[51] Int. Cl.² .............................................. C08K 5/26
[52] U.S. Cl. ......................... 260/42.46; 260/45.95 R; 260/281 N; 260/326 N; 260/326 R; 260/45.8 NE
[58] Field of Search .......... 260/281 N, 326 N, 326 R, 260/45.8 NB, 42.46, 45.95 R

[56] References Cited

U.S. PATENT DOCUMENTS

| | | | |
|---|---|---|---|
| 2,574,987 | 11/1951 | Shelley | 260/45.8 NB |
| 3,627,727 | 12/1971 | Tholstrup | 260/45.8 N |
| 3,629,189 | 12/1971 | Minagawa et al. | 260/23 |
| 3,894,990 | 7/1975 | Muller et al. | 260/45.85 B |
| 3,904,582 | 9/1975 | Hansen | 260/45.8 NB |
| 3,933,736 | 1/1976 | Yoshikawa et al. | 260/45.8 R |

*Primary Examiner*—Eugene C. Rzucidlo
*Attorney, Agent, or Firm*—Brumbaugh, Graves, Donohue & Raymond

[57] ABSTRACT

The specification relates to certain imido-oxamide-type compounds and derivatives thereof which are useful for preventing metal catalyzed oxidative degradation of polyolefins. The specification also relates to olefin homopolymer and copolymer compositions containing such compounds and derivatives thereof and to a method for enhancing the resistance of olefin homopolymers and copolymers against metal-catalyzed oxidative degradation by incorporating these compounds therein.

21 Claims, No Drawings

STABILIZED POLYOLEFIN COMPOSITION

BACKGROUND OF THE INVENTION

In the past, olefin homopolymers and copolymers have been used for a wide variety of applications, e.g., as insulation for electrical cables, wires and other electrical apparatus and as coatings for metals. Polyolefins are especially suitable for such applications because of their flexibility and high resistance to stress-cracking, and thermoembrittlement.

The polyolefins, however, are susceptible to oxidative degradation which is promoted by heat and ultraviolet light. Such degradation is further enhanced by metals which may be in intimate contact with the polymer or present within the polymer as an impurity.

Copper and its alloys, iron and certain other active metals including cobalt, manganese, nickel and chromium have particularly detrimental effects on the stability of olefin polymers. Such metals promote a catalytic degradation reaction in the polyolefins which cause the polymers to become brittle and to lose strength to the extent of mechanical failure.

Polyolefins are frequently reinforced with inorganic and mineral fillers, for example, asbestos, talc, clay, silica or the like. Such fillers usually contain metals as impurities, and the fillers, therefore, exert a catalytic effect on the oxidative degradation of the polyolefins. For example, the iron impurity in asbestos fillers has proved to be particularly detrimental to asbestos-reinforced polyolefins.

In copper cable coated with polyolefins, metal catalyzed degradation presents a particular problem. In such cables, the interstices between individual wires are filled with petroleum jelly to protect the wires from any water seepage through the polymer coating. The petroleum jelly surrounding the wires, however, tends to extract stabilizers from the polymer coating. The petroleum jelly thus reduces the availability of the stabilizers for metal deactivating purposes, and consequently, decreases the stability of the polymer coating.

In the past, various antioxidant and ultraviolet light stabilizers have been incorporated into olefin homopolymers and copolymers to inhibit normal oxidative degradation. In addition, whenever the polymer might contact metals or contain metal contaminants from fillers or other additives, various metal deactivators have also been added to the polyolefins.

A number of metal deactivators are known in the art. British Pat. No. 974,274 discloses that oxamide derivatives containing the radical

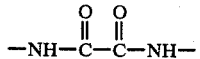

exhibit copper deactivating properties in polyolefins. Polymers and copolymers of oxamide and derivatives thereof are also discussed in the patent as being metal deactivators. Other metal deactivating oxamides having N-heterocyclic substituents are disclosed in U.S. Pat. No. 3,543,306 and in German Pat. No. 1,926,547.

Many references have recommended the use of oxalic acid derivatives as copper deactivators for various polyolefin compositions. For example, U.S. Pat. No. 3,117,104 discloses N,N'-dihydrocarbyl oxalhydrazides, where the hydrocarbyl group is selected from alkyl, aryl and naphthalene radicals. Also, U.S. Pat. No. 3,357,944 discusses oxalobis-(salicylidenehydrazide) derivatives, while U.S. Pat. No. 3,440,210 mentions N,N'-dibenzal (oxalyl dihydrazide) derivatives. Moreover, U.S. Pat. No. 3,484,285 discusses oxalyl dihydrazide and other hydrazides containing the radical

Still another group of compounds which have been used as copper deactivators is the substituted dicarboxylic acid dihydrazides described in U.S. Pat. No. 3,627,727 and the heterocyclic hydrazines and lactams described in U.S. Pat. No. 3,629,189.

A number of the prior art oxamide and oxalic acid dihydrazide metal deactivators display substantial drawbacks in certain polyolefin applications. Such metal deactivators cause adverse effects because of their incompatibility with antioxidants and stabilizers which are normally incorporated in the polyolefins. In such instances, the activity of the antioxidant is destroyed, and consequently, overall breakdown of the polymers occurs.

In other situations, the prior art metal deactivators do not readily disperse in the polyolefin polymer. As a result, they cannot be uniformly distributed throughout the composition.

Still another undesirable effect caused by some prior art metal deactivators is discoloration and staining. Such properties often render unsuitable an otherwise effective metal deactivator, i.e., for applications in which color stability is an important factor. For example, discoloration and staining must be avoided in decorative tiles for aesthetic reasons and in color-coded underground electrical cable insulation for reasons of identification.

SUMMARY OF THE INVENTION

It has now been discovered that enhanced resistance to metal-catalyzed oxidation can be imparted to olefin homopolymers and copolymers by incorporating certain compounds therein. Thus, in accordance with one embodiment of the invention, one or more of the following products are formed:

1. a compound having the structural formula:

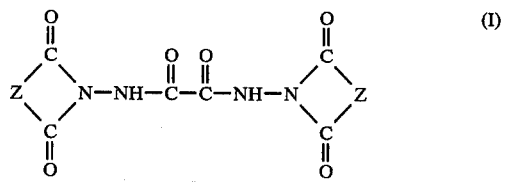

wherein Z represents a bivalent radical which together with the dicarboximide group may form a monocyclic or polycyclic ring system and is selected from the group consisting of phenylene, cyclohexylene, cyclohexenylene, cyclohexenylene substituted by a methyl group, norbornenylene, ethylene, vinylene and tetradecenylene;

2. a dimethyl sulfoxide complex of compounds of the structural formula (I) wherein Z is a bivalent radical having at least one C—C double bond and is selected from the group consisting of phenylene, vinylene, cyclohexenylene, cyclohexenylene substituted by a methyl group and norbornenylene;

3. a tertiary amide complex of the compound of the structural formula (I) wherein Z is a bivalent radical having at least one C—C double bond and is selected from the group consisting of phenylene, vinylene, cyclohexenylene, cyclohexenylene substituted by a methyl group and norbornenylene;

4. an intermediate compound having the structural formula:

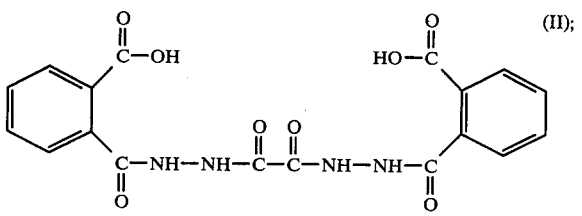

5. a tertiary-amide complex of the compound of structural formula (II);

6. a compound of the structural formula (I) in its hydrated enol form wherein Z is a phenylene radical;

7. a compound having the structural formula:

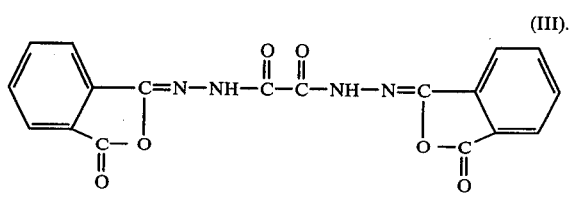

In accordance with a second embodiment of the invention, one or more of these products are combined with a polyolefin.

DETAILED DESCRIPTION OF THE INVENTION

The imido-oxamide-type compounds of the invention can be prepared by any suitable method. In one method, oxalic acid dihydrazide is reacted with a cyclic dicarboxylic anhydride in an organic solvent by the following two-step reaction:

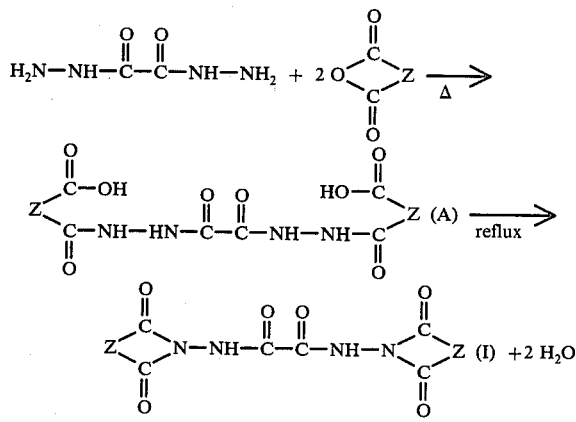

where Z is the same as defined above for formula (I).

Any cyclic dicarboxylic anhydride may be used in the reaction with oxalic dihydrazide, such as
phthalic anhydride,
succinic anhydride,
tetrapropenylsuccinic anhydride,
cyclohexane-1,2-dicarboxylic anhydride,
4-cyclohexene-1,2-dicarboxylic anhydride,
4-methyl-4-cyclohexene-1,2-dicarboxylic anhydride,
5-norbornene-2,3-dicarboxylic anhydride,
itaconic anhydride,
maleic anhydride,
1,4-cyclohexadiene-1,2-dicarboxylic anhydride,
octylsuccinic anhydride, and
1,3-cyclopentanedicarboxylic anhydride.

The above reaction can be conducted under various temperature and solvent conditions. The temperature at which the above reaction is conducted depends on the product to be isolated and the solvent which is used. Generally, hydrocarbons are used as solvents. The preferred hydrocarbons are the aromatic hydrocarbons, such as toluene or xylene.

The second (cyclodehydration) step in the above reaction proceeds at a faster rate if the reaction is conducted in a hydrocarbon solvent admixed with a tertiary amide or dimethyl sulfoxide. The tertiary amides and dimethyl sulfoxide may form complexes with the compounds of formula (I) and formula (A) and thus facilitate the removal of water.

If hydrocarbon alone is used as solvent, the cyclodehydration step in the above reaction can also be increased by conducting the reaction in the presence of an acid catalyst. The preferred acid catalysts are the organic sulfonic acids.

The tertiary amide and dimethyl sulfoxide complexes of the compounds of formula (I) and formula (A) can be prepared by two basic methods:

Method I: Oxalic dihydrazide and a cyclic dicarboxylic anhydride are reacted in excess tertiary amide or dimethyl sulfoxide in the presence of an appropriate solvent. The preferred solvent is a hydrocarbon, such as toluene.

Method II: Oxalic dihydrazide and a cyclic dicarboxylic anhydride are reacted and the product of formula (I) is isolated as described above. The product is then reacted with two molar equivalents of tertiary amide or dimethyl sulfoxide in a hydrocarbon solvent.

In the formation of the complexes of the present invention, the preferred tertiary amides are N-methyl-2-pyrrolidone, N,N-dimethylformamide, N,N-dimethylacetamide and N-methylpiperidone.

The intermediate compound designated as formula (A) can be isolated by controlling the reaction temperature and selecting the appropriate solvent. For example, oxalic acid bis[2-(2'-carboxybenzoyl)hydrazide] can be prepared by reacting oxalic dihydrazide and phthalic anhydride in glacial acetic acid at about 80° C.

The final product (I) can be obtained without isolating the intermediate (A) by subsequently conducting the thermal cyclodehydration step in situ.

Tertiary amide complexes of the intermediate of formula (A) can also be prepared according to Method I described above by controlling the reaction temperature so that the cyclodehydration step does not occur. For instance, the N-methyl-2-pyrrolidone complex of oxalic acid bis[2-(2'-carboxybenzoyl)hydrazide] can be prepared by reacting oxalic acid dihydrazide and phthalic anhydride in N-methyl-2-pyrrolidone and a hydrocarbon solvent at about 80° C.

The compounds for formula (I) in which Z has aromatic unsaturation can be converted from their keto form to their hydrated enol form by hydrolyzing isolated tertiary amide or dimethyl sulfoxide complexes of such compounds. Tertiary amide and dimethyl sulfoxide complexes of the compounds of formula (I) in which Z does not have aromatic unsaturation remain in their keto form upon hydrolysis.

The reaction for the N-methyl-2-pyrrolidone complex of N,N'-bis(phthalimido)oxamide is illustrated below:

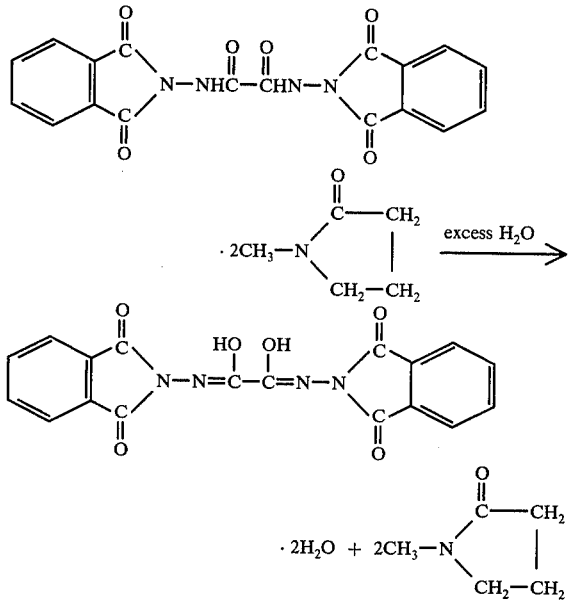

The hydrated enol form of the compounds of formula (I) in which Z has aromatic unsaturation can also be obtained without isolating the complex by preparing the tertiary amide or dimethyl sulfoxide complex by Method I described above and subsequently conducting hydrolysis in situ.

Polyolefins can be stabilized by incorporating the imido-oxamide-type compounds of the invention into the polymer compositions. Any suitable amount can be incorporated into such a composition. A particularly effective range is 0.01 to 5.0 parts, preferably 0.1 to 2.0 parts, compound of the invention per hundred parts of polyolefin.

The polyolefins employed in the composition of the present invention include polymers of, among others, straight chain olefins having 2 to 10 carbon atoms, such as ethylene, propylene, 1-butene, 1-octene, and 1-decene; branched olefins having 2 to 10 carbon atoms, such as 3-methyl-1-butene, 4-methyl-1-pentene; and mixtures thereof. Such homopolymers or copolymers may be either the low density or high density type. These polymers can be prepared by methods well-known in the art.

The polyolefin composition of the invention may also contain known optional ingredients. These include, among others, fillers, pigments, ultraviolet light stabilizers, thermal stabilizers, processing lubricants and antioxidants.

The stabilizers suitable for use in the polyolefin compositions include, among others, phenols; organic phosphites; phosphates, thiophosphites, or thiophosphates of dialkyl hydroquinone; and thio acid esters and their metal salts. More specifically, the phenol stabilizers may contain one or more phenolic hydroxyl groups. Such phenol stabilizers may have a sterically hindered or polynuclear structure. With the bicyclic phenol stabilizers, the rings can be linked together by thio, oxyether, alkylene, alicyclidene or arylidene groups. Representative phenol stabilizers include, among others 2,4-di-t-butylphenyl 3,5-di-t-butyl-4-hydroxybenzoate; 4,4'-butylidenebis-(6-t-butyl-m-cresol); 4,4'-oxybis-(3-methyl-6-isopropylphenol); 2,6-di-t-butyl-p-cresol; and resorcinol and its 4-alkyl derivatives.

The organic phosphite stabilizers that may be incorporated into the polyolefin compositions may have one or more organic radicals attached to the phosphorus atom through an oxygen atom. Compounds have bivalent organic radicals forming a heterocyclic ring with the phosphorus atom are also suitable. Exemplary organic phosphites are, among others, phenyl di-2-ethylhexyl phosphite, tridodecyl phosphite, diphenyl phosphite and from the phenolic phosphites, bis[4,4'-thiobis(2-t-butyl-5-methylphenol)]#isooctyl phosphite.

The satisfactory phosphates, thiophosphites, or thiophosphates of dialkyl hydroquinone include, among others, 3,5-di-t-butyl-4-hydroxyphenyl phosphate, 3,5-di-t-butyl-4-hydroxyphenyl thiophosphite, 3-methyl-5-t-butyl-4-hydroxyphenyl thiolophosphate, and di-n-amyl(α-methyl-3-ethyl-5-isopropyl-4-hydroxybenzyl)-phosphonate. Distearyl thiodipropionate, among others, is a satisfactory thio acid ester.

The ultraviolet light stabilizers that can be used in the polyolefin composition include, among others, 2-hydroxybenzophenones, o-hydroxyphenylbenzotriazoles and 1,3,5-triazines.

The preferred antioxidants that can be employed in the polyolefin composition of the present invention are, among others, the trishydroxyphenylpropane derivatives described in U.S. Pat. No. 3,196,185 (which is incorporated herein by reference) and the alkanol or alkane polyol esters of dilower alkyl hydroxyphenylalkanoic acid described in U.S. Pat. No. 3,285,855 (which is incorporated herein by reference). The preferred member of the latter group of compounds is tetrakis[methylene-3-(3',5'-di-t-butyl-4'-hydroxyphenyl)propionate]methane. Still another group of antioxidants that can be utilized in the polyolefin composition is the isocyanurates, such as, tris(3,5-di-t-butyl-4-hydroxybenzyl)isocyanurate and tris[β-[β'-(3,5-di-t-butyl-4-hydroxyphenyl)propionyloxy]-ethyl]isocyanurate.

Thus, in accordance with the present invention, the imido-oxamide type compounds of the invention possess metal deactivating properties. The compounds are particularly effective as deactivators in polyolefin homopolymers and copolymers which are in contact with copper. Moreover, the compounds of the invention are effective deactivators of copper, iron, cobalt, manganese, nickel and chromium, all of which are commonly found in mineral fillers, such as asbestos, talc and other silicate minerals. Furthermore, the imido-oxamide-type compounds of the invention exhibit good compatibility with many antioxidants and stabilizers, and they do not discolor or stain polyolefin compositions. The compounds of the invention also readily disperse in polyolefin compositions.

Some of the products of the invention are used as intermediates in the preparation of compounds possessing such metal deactivating properties and in the preparation of polymers for coatings and insulating materials.

The following examples are intended to illustrate but not to limit the invention. Unless otherwise stated, all parts and percentages in the specification and claims are by weight.

EXAMPLE 1

Two moles of phthalic anhydride (296g) and one mole of oxalic dihydrazide (118 g) in xylene (2.5 l) were heated at reflux until two moles of water were removed (about 24 hours). The product was filtered and dried at 50° C. N,N'-bis(phthalimido)-oxamide was obtained in 94-6 percent yield. The compound was a white solid melting at 295° C (dec.) and having the following elemental analysis by weight percent:

| $C_{18}H_{10}N_4O_6$ | theoretical | Found |
|---|---|---|
| Carbon | 57.15 | 56.85 |
| Hydrogen | 2.66 | 2.87 |
| Nitrogen | 14.81 | 14.85 |

The compound is characterized by infrared bands at 5.6(w), 5.8(s) and 5.9(s)$\mu$.

EXAMPLE 2

Two moles of cyclohexane-1,2-dicarboxylic anhydride (308 g.) and one mole oxalic dihydrazide (118 g.) in 500 ml. N-methyl-2-pyrrolidone and 500 ml. toluene were heated at reflux until two moles of water were removed (about 2 hours). The reaction mixture was diluted with benzene and filtered. The product was washed with benzene and dried at 50° C. to give white crystalline N,N'-bis(cyclohexane-1,2-dicarboximido)oxamide in 78% yield. Treatment of the filtrate with water gave an additional 15% of the product, total yield 93%. The product melted and decomposed at 300° C.

EXAMPLE 3

Two moles (533 g.) tetrapropenylsuccinic anhydride and one mole (118 g.) oxalic dihydrazide in 5 l. xylene was heated at reflux until two moles of water was removed (about four hours). The solution was filtered to remove solids and the solvent was then removed by evaporation leaving tacky, resinous product, identified by infrared spectra as N,N-bis-(tetrapropenylsuccinimido)oxamide.

EXAMPLE 4

Two moles (200 g.) of succinic anhydride and one mole (118 g.) of oxalic dihydrazide in 750 ml. N-methyl-2-pyrrolidone and 500 ml. toluene were heated at reflux until water evolution was complete (about 4 hours). Upon cooling, a crystalline complex separated. The mixture was diluted with benzene and then filtered. After drying at 50° C, the complex was treated with water to give N,N'-bis(succinimido)oxamide, having a melting point of >310° C. The overall yield was about 49%.

EXAMPLE 5

Two moles of phthalic anhydride (296 g.) and one mole of oxalic dihydrazide (118 g.) in 500 ml. N-methyl-2-pyrrolidone and 500 ml. toluene were heated at reflux until two moles of water were removed (about 2 hours). The mixture was diluted with benzene and filtered. After washing with benzene, the white product was dried to constant weight at 50° C giving an essentially quantitative yield of N,N'-bis(phthalimido)oxamide-N-methyl-2-pyrrolidone 1:2 complex.

The N-methyl-2-pyrrolidone complex of N,N'-bis(4-cyclohexene-1,2-dicarboximido)oxamide was prepared by an analogous method.

EXAMPLE 6

Two moles of phthalic anhydride (296 g.) and one mole of oxalic dihydrazide (118 g.) in 500 ml. dimethyl sulfoxide and 750 ml. toluene were heated at reflux until two moles of water were removed (about 2 hours). The mixture was cooled and filtered. After washing with benzene, the white product was dried to constant weight at 50° C giving an essentially quantitative yield of N,N'bis(phthalimido)oxamide #-# dimethyl sulfoxide 1:2 complex.

The dimethyl sulfoxide complex of N,N'-bis(5-norbornene-2,3-dicarboximido)oxamide was prepared by the same method.

EXAMPLE 7

Two moles of maleic anhydride (196 g.) and 2.1 moles isoprene (143 g.) were reacted in 500 ml. N-methyl-2-pyrrolidone and 625 ml. toluene until the exothermic reaction had subsided. One mole oxalic dihydrazide (118 g.) was added and the mixture was heated at reflux until two moles of water were removed (about 2 hours). The resulting solution was cooled and added to 4 l. distilled water to hydrolyze the complex. The resulting white solid was filtered, washed with water and then dried at 50° C giving an 89% yield on N,N'-bis(4-methyl-4-cyclohexene-1,2-dicarboximido)oxamide, m.p. 240°–250° C.

EXAMPLE 8

N,N'-bis(4-cyclohexene-1,2-dicarboximido)oxamide-N-methyl-2-pyrrolidone 1:2 complex prepared by the method described in Example 5 was stirred with water for one-half hour. The product was filtered, washed and dried at 50° C giving a white, crystalline solid, N,N'-bis(4-cyclohexene-1,2-dicarboximido)-oxamide melting at 263°–275° C. (decomposes).

EXAMPLE 9

N,N'-bis(5-norbornene-2,3-dicarboximido)oxamide-dimethyl sulfoxide 1:2 complex (25 g.) prepared according to Example 5 was stirred with 250 ml. water for 15 minutes, filtered and dried at 110° C. A 94.5% yield (17.1 g.) of white solid, N,N'-bis(5-norbornene-2,3-dicarboximido)oxamide melting at 304°–308° C. (decomposed) was obtained.

EXAMPLE 10

N,N'-bis(phthalimido)-oxamide-N-methyl-2-pyrrolidone 1:2 complex prepared by the method described in Example 5 was stirred with water for one-half hour. The product was filtered, washed and dried at 50° C. giving a white, crystalline solid, melting (decomposed) at 295°–298° C. The infrared spectra is indicative of the enol form of N,N'-bis(phthalimido)oxamide, i.e., the spectra displays an —OH band at 2.9$\mu$ replacing the —NH band at 3.1$\mu$ and some differences in the carbonyl spectra at 5.8–8.9$\mu$ are also evident. Two moles of water are present as confirmed by Karl Fisher analysis yielding 8.06% $H_2O$ (8.70% theory). At temperatures above 105° C., the water of hydration is driven off and the keto form is obtained as confirmed by infrared spectra.

EXAMPLE 11

Two moles of phthalic anhydride (296 g.) and one mole of oxalic dihydrazide (118 g.) in 500 ml. N-methyl-2-pyrrolidone and 1 l. toluene were heated at reflux until water evolution was complete (about 2 hours). The mixture was cooled to room temperature. One l. of water was added to hydrolyze the complex and the product was isolated by filtration. Drying at 50° C. gave a 93.6% yield of hydrated N,N'-bis(phthalimido)oxamide enol form. Similar experiments using N,N-dimethyl-acetamide and dimethyl sulfoxide, instead of N-methyl-2-pyrrolidone gave yields of 95.0% and 95.3%, respectively.

EXAMPLE 12

In an alternate method, one mole N,N'-bis(phthalimido)-oxamide (378 g.) prepared according to the method of Example 1 and excess N-methyl-2-pyrrolidone (198 g.) in two liters toluene were heated at 70° C. After cooling, the complex was filtered, washed and dried at 50° C. N,N'-bis(phthalimido)oxamide-N-methyl-2-pyrrolidone 1:2 complex was obtained in 96% yield.

The following compounds were prepared in an analogous manner:
1. N,N'-bis(phthalimido)oxamide — dimethylformamide 1:2 complex
2. N,N'-bis(phthalimido)oxamide — dimethylacetamide 1:2 complex.

EXAMPLE 13

One mole of oxalic dihydrazide (118 g.) and two moles of phthalic anhydride (296 g.) in 500 ml. N-methyl-2-pyrrolidone and 500 ml. toluene were reacted at 80° C. for 1 hour. After cooling, the reaction product was filtered and dried at 50° C. A white solid, oxalic acid bis[2-(2'-carboxybenzoyl)hydrazide]-N-methyl-2-pyrrolidone 1:2 complex was obtained in quantitative yield.

EXAMPLE 14

One mole of oxalic dihydrazide (118 g.) and two moles of phthalic anhydride (296 g.) in glacial acetic acid (2 kg.) were reacted at 80° C for 1 hour. After cooling, the reaction product was filtered and dried at 50° C. A white solid oxalic acid bis[2-(2'-carboxybenzoyl)hydrazide] melting at 265° C and decomposing at 294° C was obtained in quantitative yield.

EXAMPLE 15

Oxalic acid bis[2-(2'-carboxybenzoyl)hydrazide] prepared according to Example 14 is heated at 200° C until weight loss due to $H_2O$ evolution is complete (about 2 hours) giving a white crystalline product melting at 294° to 300° C (decomposes). This compound is characterized by infrared bands at 5.6(w), 5.8(s), 6.0(s) and 6.2μ.

Alternatively, N'N'-bis(isophthalimido)oxamide can be prepared by heating under the above conditions, oxalic acid bis[2-(2'-carboxybenzoyl)hydrazide] N-methyl-2-pyrrolidone complex prepared according to Example 13.

EXAMPLE 16

One hundred parts of unstabilized low density polyethylene (DYNK-1 manufactured by Union Carbide), 0.1 parts tetrakis[methylene-3-(3',5'-di-t-butyl-4'-hydroxyphenyl) propionate]methane antioxidant (Irganox 1010 manufactured by Ciba-Geigy), and 0.1 parts of various imido-oxamide-type compounds of the invention were compounded at 138° C on a two roll mill, sheeted off as 30 mm. sheets, and subsequently compression molded to a 15 mm. thickness. Conditioned 80 mesh copper screens (aged 24 hours at 140° C) were sandwiched between two of the polyethylene sheets and compression molded to 20-25 mm. under a pressure of 6,000 p.s.i. The pressed specimens were cut into 2 by 2 inch specimens so that the cross section of the copper screen became exposed. The specimens were then aged in in an air oven at 150° C. A control containing 100 parts low density polyethylene and 0.1 parts of the antioxidant was also prepared and treated in the same manner.

The copper catalyzed degradation of the polymer composition was determined by visual inspection. The initial point of degradation was indicated by the appearance of black spots and the final point by the blackening and embrittlement of the sample. Table I illustrates the results of these tests.

TABLE I

Stabilization of Low Density Polyethylene in Contact with Copper

| Imido-Oxamide-Type Compound | Contacting Conditioned Copper | |
|---|---|---|
| | Hours to Initial Degradation | Hours to Total Degradation |
| None (Control) | 121 | 169 |
| N,N'-bis(phthalimido)oxamide | 508 | 604 |
| N,N'-bis(tetrapropenylsuccinimido)oxamide | 316 | 460 |
| N,N'-bis(cyclohexane-1,2-dicarboximido)-oxamide | 329 | 377 |
| N,N'-bis(4-methyl-4-cyclohexene-1,2-dicarboximido)oxamide | 353 | 401 |
| N,N'-bis(4-cyclohexene-1,2-dicarboximido)-oxamide | 520 | 568 |
| N,N'-bis(5-norbornene-2,3-dicarboximido)-oxamide | 425 | 496 |
| N,N'-bis(phthalimido)oxamide-N-methyl-2-pyrrolidone 1:2 complex | 329 | 544 |
| N,N'-bis(4-cyclohexene-1,2-dicarboximido)-oxamide-N-methyl-2-pyrrolidone 1:2 complex | 401 | 520 |
| N,N'-bis(5-norbornene-2,3-dicarboximido)-oxamide-N-methyl-2-pyrrolidone 1:2 complex | 353 | 449 |
| N,N'-bis(phthalimido)oxamide, hydrated enol form | 544 | 641 |
| N,N'-bis(isophthalimido)oxamide | 568 | 641 |

The results demonstrate that the compositions containing the imido-oxamide-type compounds of the invention remain free from deterioration for about 316 to 568 hours, while the composition containing no such compound begin to deteriorate within 121 hours.

EXAMPLE 17

One hundred parts of unstabilized high density polyethylene (Alathon 5496 manufactured by E.I. du Pont de Nemours & Co.), 0.2 parts antioxidant (Irganox 1010 manufactured by Ciba-Geigy), and 0.1 parts of an imido-oxamide-type compound of the invention were compounded at 129° C. on a two roll mill, and sheeted off as about 62 mm. sheets. Subsequently, the sheets were compression molded to a 15 mm. thickness under 100 ton pressure for five minutes at 171° C. A control containing 100 parts of the high density polyethylene and 0.2 parts of the antioxidant was similarly prepared.

Eighty mesh copper screen was conditioned by degreasing in hexane and oven aging for 24 hours at 140° C. The conditioned screen was sandwiched between two of the polyethylene sheets and compression molded to 20–25 mm. under pressure of 5 tons for 5 minutes at 171° C. The pressed specimens were cut into 2 by 2 inch specimens so that the cross section of the copper screen became exposed. The specimens were then aged in an air circulating oven at 140° C. The initial and final points of degradation were determined as in Example 16.

Columns 2 and 3 of Table II list the results of these tests using the imido-oxamide-type compounds of the invention as indicated in column 1.

TABLE II

Stabilization of High Density Polyethylene in Contact with Copper

| Imido-Oxamide-Type Compound | Contacting Conditioned Copper | |
|---|---|---|
| | Hours to Initial Degradation | Hours to Total Degradation |
| None (Control) | 369 | 414 |
| N,N'-bis(phthalimido)oxamide-DMSO 1:2 complex | 1123 | 1255 |
| N,N'-bis(phthalimido)oxamide | 1123 | 1291 |

The results shown in Table II demonstrate that high density polyethylene stabilized with the imido-oxamide-type compound of the invention remains free from deterioration 2 to 3 times longer than compositions not containing such compound.

EXAMPLE 18

One hundred parts of unstabilized polypropylene (Profax 6501 manufactured by Hercules Incorporated), was compounded on a two roll mill at 138° C with 0.2 parts tetrakis-[methylene-3-(3',5'-di-t-butyl-4'-hydroxyphenyl)propionate]-methane (Irganox 1010 manufactured by Ciba-Geigy), and varying amounts N,N'-bis(phthalimido)oxamide as indicated in the first column of Table III below. After milling, the sample was worked in a Brabender Plasti-Corder at 190° C, sheeted off as 30 mm. sheets, and subsequently, compression molded to a 15 mm. thickness.

Eighty mesh copper screens, conditioned by aging for 24 hours at 140° C, were sandwiched between two sheets, and the sheets were compression molded to 20–25 mm. under a pressure of 6,000 p.s.i. The pressed specimens were cut into 2 by 2 inch specimens so that the cross section of the copper screen became exposed. The specimens were then aged in an air oven at 150° C.

The copper catalyzed degradation of the polypropylene composition was determined by visual inspection. The initial point of degradation was indicated by the appearance of embrittlement and yellow crystals on the surface of the specimen, while the final point was indicated by the disintegration of the specimen. The results of these tests are listed in the second and third columns of Table III hereinbelow.

TABLE III

Stabilization of Polypropylene in Contact with Copper

| N,N-bis(phthalimido)oxamide, parts per hundred | Contacting Conditioned Copper | |
|---|---|---|
| | Hours to Initial Degradation | Hours to Total Degradation |
| None | 473 | 570 |
| 0.1 | 760 | 856 |
| 0.2 | 760 | 906 |

The results shown in Table III illustrate that the imido-oxamide-type compound of the invention provides excellent protection against copper-catalyzed degradation of polypropylene. The specimens containing the imido-oxamide-type compound were protected from degradation for 760 hours, while specimens containing none of the compound started to degrade in about 473 hours.

EXAMPLE 19

Compositions B, C and D were prepared by compounding high density polyethylene, antioxidant, and N,N-bis(phthalimido)-oxamido in the proportions indicated in Table IV. These compositions were formed into sheets and copper screen was sandwiched between two of these sheets by the method described in Example 17. The pressed specimens were cut into ¾ by 1 inch specimens so that the cross section of the copper screen became exposed.

TABLE IV

| Components in Parts | Composition B | Composition C | Composition D |
|---|---|---|---|
| High density Polyethylene[a] | 100.00 | 100.00 | 100.00 |
| Antioxidant[b] | — | 0.1 | 0.1 |
| N,N'-bis(phthalimido)oxamide | — | — | 0.1 |

[a] Alathon 5496 manufactured by E.I. du Pont de Nemours & Co.
[b] Irganox 1010 manufactured by Ciba-Geigy.

The specimens for each composition were divided into three groups and each group was given different preliminary treatment. The first group was not subjected to any preliminary treatment. The second and third groups were provided with a stainless steel wire holder. The second group was then immersed for one minute in an unstabilized petroleum jelly, and the third group was immersed for one minute in a stabilized petroleum jelly.

After allowing excess jelly to drip off those specimens treated with the jelly, all the specimens were oven aged for 10 days at 70° C. After aging, excess jelly, if used, was wiped from the surface of the specimens leaving a thin film on the surface. The specimens were then subjected to the oven aging tests at 140° C as described above in Example 17. The results are summarized in Table V herein below.

TABLE V

Stabilization of High Density Polyethylene in Contact with Copper and Petroleum Jelly

| Test Conditions | Composition B Initial | Composition B Final | Composition C Initial | Composition C Final | Composition D Initial | Composition D Final |
|---|---|---|---|---|---|---|
| No exposure to petroleum jelly | 21 | 45 | 358 | 382 | 887 | 990 |
| After exposure to unstabilized petroleum jelly[c] | 17 | 41 | 161 | 211 | 425 | 522 |
| After exposure to stabilized petroleum jelly[d] | 17 | 41 | 161–185 | 211 | 594 | 666 |

[c]Witco 13 manufactured by Witco Chemical Company.
[d]Witco 13C manufactured by Witco Chemical Company.

EXAMPLE 20

The procedure of Example 19 was repeated except that polypropylene resin was used instead of high density polyethylene and the petroleum jelly-treated specimens were oven aged at 150° C. The amounts of polypropylene, antioxidant and N,N'-bis(phthalimido)-oxamide in each composition tested are indicated in Table VI below and the results are complied in Table VII.

TABLE VI

| Components in Parts | Composition E | Composition F |
|---|---|---|
| Polypropylene[a] | 100.0 | 100.0 |
| Antioxidant[b] | 0.2 | 0.2 |
| N,N'-bis(phthalimido)oxamide | — | 0.1 |

[a]Profax 6501 manufactured by Hercules Incorporated.
[b]Irganox 1010 manufactured by Ciba-Geigy.

Table VII

Stabilization of Polypropylene in Contact with Copper and Petroleum Jelly

| Test Conditions | Composition E Initial | Composition E Final | Composition F Initial | Composition F Final |
|---|---|---|---|---|
| No exposure to petroleum jelly | 473 | 570 | 821 | 969 |
| After exposure to unstabilized petroleum jelly[c] | 599 | 719 | 851 | 947 |
| After exposure to stabilized petroleum jelly[d] | 660 | 683 | 985 | 1045 |

[c]Witco 13 manufactured by Witco Chemical Company.
[d]Witco 13C manufactured by Witco Chemical Company.

EXAMPLE 21

Unstabilized-ethylene-propylene copolymer, antioxidant and N,N'-bis(phthalimido)oxamide were compounded in the proportions indicated in Table VIII. A copolymer composition containing only the antioxidant (composition G in Table VIII) was run as a control. The compositions were tested according to the procedure set out in Example 19, and the results are compiled in Table IX.

TABLE VIII

| Components in Parts | Composition G | Composition H |
|---|---|---|
| Ethylene-propylene copolymer[a] | 100.0 | 100.0 |
| Antioxidant[b] | 0.2 | 0.2 |
| N,N'-bis(phthalimido)oxamide | — | 0.1 |

[a]Profax SB 272 manufactured by Hercules Incorporated.
[b]Irganox 1010 manufactured by Ciba-Geigy.

TABLE IX

Stabilization of Ethylene-Propylene Copolymer in Contact with Copper and Petroleum Jelly

| Test Conditions | Composition G Initial | Composition G Final | Composition H Initial | Composition H Final |
|---|---|---|---|---|
| No exposure to petroleum jelly | 742 | 814 | 2337 | 2441 |
| After exposure to unstabilized petroleum jelly[c] | 233 | 329 | 1343 | 1489 |
| After exposure to stabilized petroleum jelly[d] | 329 | 402 | 1573 | 1727 |

[c]Witco 13 manufactured by Witco Chemical Company.
[d]Witco 13C manufactured by Witco Chemical Company.

It can be inferred from the results in Tables V, VII and IX above that the imido-oxamide-type compounds of the invention are not extracted substantially from the polyethylene, polypropylene or ethylene-propylene copolymer compositions by petroleum jelly similar to that used in cable applications. Moreover, even under the adverse conditions used in Examples 19, 20 and 21, the compounds of the invention afford good copper deactivating activity.

EXAMPLE 22

Antioxidant-containing polypropylene, asbestos filler and N,N'-bis(phthalimido)oxamide were compounded in the proportions listed in Table X to form compositions J, K, L, M, N and O. These compounds were tested according to the procedures set out in Example 17. The results of these tests are compiled in Table XI.

TABLE X

| Components in Parts | J | K | L | M | N | O |
|---|---|---|---|---|---|---|
| Polypropylene[a] | 100.0 | 100.0 | 100.0 | 100.0 | 100.0 | 100.0 |
| Asbestos[b] | — | 10.0 | 10.0 | 10.0 | 10.0 | 10.0 |
| N,N'-bis(phthalimido)oxamide | — | — | 0.1 | 1.0 | 3.0 | 5.0 |

[a]Profax 6523 manufactured by Hercules Incorporated
[b]Carey 7R3 manufactured by Carey-Canadian Mines Ltd.

TABLE XI

Stabilization of Asbestos-filled Polypropylene

| Oven Aged at 150° C | J | K | L | M | N | O |
|---|---|---|---|---|---|---|
| Hours to initial failure | >1000 | 17 | 90 | 474 | 666 | 682 |
| Hours to total failure | | 34 | 121 | 522 | 723 | 771 |

The results shown in Table XI demonstrate that the compound of the invention is effective in deactivating metal impurities present in asbestos-filled polypropylene.

EXAMPLE 23

Antioxidant-containing polypropylene was compounded with various talc fillers and N,N'-bis(phthalimido)oxamide in the proportions listed in Table XII to form compositions P, Q, R, S and T. These compositions were then tested by the procedures set out in Example 17. The results of these tests are compiled in Table XIII.

TABLE XII

| Components in Parts | Composition | | | | |
|---|---|---|---|---|---|
| | P | Q | R | S | T |
| Polypropylene[a] | 100.0 | 100.0 | 100.0 | 100.0 | 100.0 |
| Talc[b] | — | 40.0 | 40.0 | — | — |
| Talc[c] | — | — | — | 40.0 | 40.0 |
| N,N'-bis(phthalimido)oxamide | — | — | 0.1 | — | 0.1 |

[a]Profax 6523 manufactured by Hercules Incorporated.
[b]NYTAL 100 manufactured by R. T. Vanderbilt Company, Inc.
[c]Fibertal 1 manufactured by R. T. Vanderbilt Company, Inc.

TABLE XIII

| Stabilization of Talc-filled Polypropylene | | | | | |
|---|---|---|---|---|---|
| | Composition | | | | |
| Oven Aged at 150° C | P | Q | R | S | T |
| Hours to initial failure | >600 | 78 | 149 | 23 | 126 |
| Hours to total failure | | 134 | 173 | 69 | 173 |

These results demonstrate that the compound of the invention is an effective deactivator of metal impurities present in talc-filled polypropylene.

Having set forth the general nature and specific embodiments of the present invention, the true scope is now particularly pointed out in the appended claims.

I claim:

1. A compound having the structural formula:

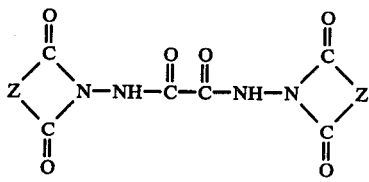 (I)

wherein Z is a bivalent radical which together with the dicarboximide group forms a monocyclic or polycyclic ring system and is selected from the group consisting of phenylene, cyclohexylene, cyclohexenylene, cyclohexenylene substituted by a methyl group, norbornenylene, ethylene, vinylene and tetradecenylene.

2. The compound according to claim 1 which is N,N'-bis(phthalimido)oxamide.

3. The compound according to claim 1 which is N,N'-bis(cyclohexane-1,2-dicarboximido) oxamide.

4. The compound according to claim 1 which is N,N'-bis(tetrapropenylsuccinimido) oxamide.

5. The compound according to claim 1 which is N,N'-bis(succinimido)oxamide.

6. The compound according to claim 1 which is N,N'-bis(4-methyl-4-cyclohexene-1,2-dicarboximido)oxamide.

7. The compound according to claim 1 which is N,N-bis(4-cyclohexene-1,2-dicarboximido) oxamide.

8. The compound according to claim 1 which is N,N'-bis(5-norbornene-2,3-dicarboximido) oxamide.

9. A process for preparing a compound of the formula

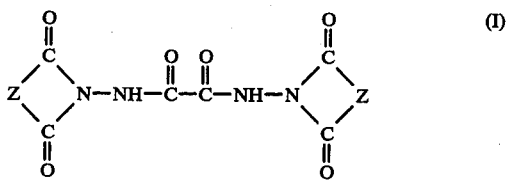 (I)

wherein Z is a bivalent radical, which together with the dicarboximide group forms a monocyclic or polycyclic ring system and is selected from the group consisting of phenylene, cyclohexylene, cyclohexenylene, cyclohexenylene substituted by a methyl group, norbornenylene, ethylene, vinylene and tetradecenylene, which comprises reacting oxalic acid dihydrazide and a cyclic dicarboxylic anhydride of the formula

 (IV)

wherein Z is a bivalent radical as defined above, in a molar ratio of one part oxalic acid dihydrazide to two parts cyclic dicarboxylic anhydride in the presence to a hydrocarbon solvent to form a reaction mixture containing an intermediate of the formula

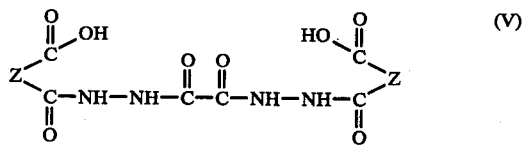 (V)

wherein Z is defined as above; refluxing the reaction mixture to dehydrocylclize the intermediate of formula (V) and form the compound of formula (I); filtering the reaction mixture to isolate a residue which is the compound of formula (I) and drying the residue.

10. A process for preparing a compound of the formula

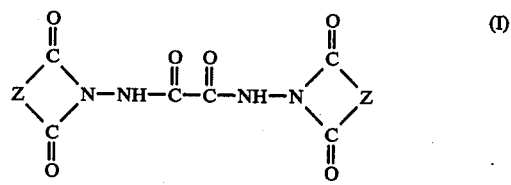 (I)

wherein Z is a bivalent radical having at least one C-C double bond and is selected from the group consisting of phenylene, vinylene, cyclohexenylene, cyclohexenylene substituted by a methyl group and norbornenylene, which comprises reacting oxalic acid dihydrazide and a cyclic dicarboxylic anhydride of the formula

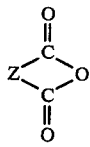

wherein Z is a bivalent radical as defined above, in a molar ratio of one part oxalic acid dihydrazide to two parts cyclic dicarboxylic anhydride in the presence of a hydrocarbon/tertiary amide solvent, wherein the tertiary amide is selected from the group consisting of N-methyl-2-pyrrolidone, N,N-dimethylformamide, N,N-dimethylacetamide and N-methyl piperidone, to form a reaction mixture containing an intermediate of the formula

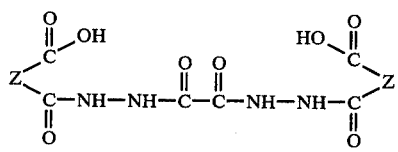

wherein Z is defined as above; refluxing the reaction mixture to dehydrocyclize the intermediate of formula (V) and form the tertiary amide complex of the compound of formula (I); hydrolyzing the tertiary amide complex to form the free compound of formula (I); filtering the hydrolyzed reaction mixture to isolate a residue which is the compound of formula (I) and drying the residue.

11. A process for preparing a compound of the formula

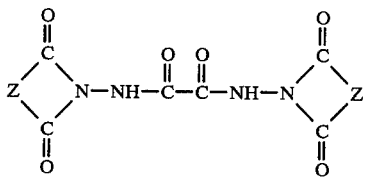

wherein Z is a bivalent radical having at least one C-C double bond and is selected from the group consisting of phenylene, vinylene, cyclohexenylene, cyclohexenylene substituted by a methyl group and norbornenylene; which comprises reacting oxalic acid dihydrazide and a cyclic dicarboxylic anhydride of the formula

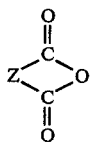

wherein Z is a bivalent radical as defined above, in a molar ratio of one part oxalic acid dihydrazide to two parts cyclic dicarboxylic anhydride in the presence of a hydrocarbon/dimethyl sulfoxide solvent to form a reaction mixture containing an intermediate of the formula

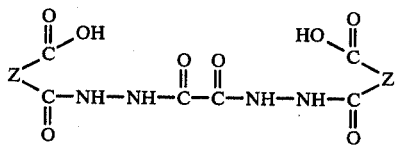

wherein Z is defined as above; refluxing the reaction mixture to dehydrocyclize the intermediate of formula (V) and form the dimethyl sulfoxide complex of the compound of formula (I); hydrolyzing the dimethyl sulfoxide complex to form the free compound of formula (I); filtering the hydrolyzed reaction mixture to isolate a residue which is the compound of formula (I) and drying the residue.

12. A composition having enhanced resistance to metal-catalyzed oxidation comprising a polyolefin having 2 to 10 carbon atoms in each olefin unit and an amount effective to impart resistance to metal-catalyzed oxidation of at least one compound having the structural formula:

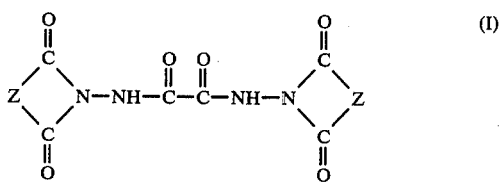

wherein Z is a bivalent radical which together with the dicarboximide group forms a monocyclic or polycyclic ring system and is selected from the group consisting of phenylene, cyclohexylene, cyclohexenylene, cyclohexenylene substituted by a methyl group, norbornenylene, ethylene, vinylene and tetradecenylene.

13. The composition according to claim 12 in which the compound is present in the amount of from about 0.01 to about 5.0 parts per hundred parts polyolefin.

14. The composition according to claim 12 in which the polyolefin is polyethylene.

15. The composition according to claim 12 in which the polyolefin is polypropylene.

16. The composition according to claim 12 in which the polyolefin is ethylene-propylene copolymer.

17. The composition according to claim 12 which further comprises an antioxidant.

18. The composition according to claim 17 in which the antioxidant is tetrakis[methylene-3-(3',5'-di-t-butyl-4'-hydroxyphenyl)propionate]methane.

19. The composition according to claim 12 which further comprises a filler.

20. The composition according to claim 19 in which the filler is selected from the group consisting of asbestos and talc.

21. A process for stabilizing polyolefins against metal-catalyzed oxidation comprising compounding a polyolefin having 2 to 10 carbon atoms in each olefin unit and an amount effective to stabilize polyolefins against metal-catalyzed oxidation of at least one compound having the structural formula:

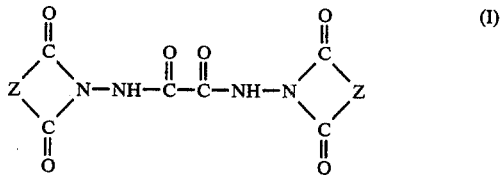

wherein Z is a bivalent radical which together with the dicarboximido group forms a monocyclic or polycyclic ring system and is selected from the group consisting of phenylene, cyclohexylene, cyclohexenylene, cyclohexenylene substituted by a methyl group, norbornenylene, ethylene, vinylene and tetradecenylene.

* * * * *

UNITED STATES PATENT OFFICE
CERTIFICATE OF CORRECTION

Patent No. 4,100,132           Dated July 11, 1978

Inventor(s) Harry Elwyn Hill

It is certified that error appears in the above-identified patent and that said Letters Patent are hereby corrected as shown below:
SUPPLEMENTAL CERTIFICATE OF CORRECTION Column 1, line 21, "cause" should read --causes--;

Column 6, line 15-16, "bis[4,4'-thiobis(2-t-butyl-5-methyl-phenol)]#isooctyl phosphite." should read --bis[4,4'-thiobis(2-t-butyl-5-methylphenol)]isooctyl phosphite.--;

Column 7, line 41-42, "N,N-bis-(tetrapropenylsuccinimido)-oxamide" should read --N,N'-bis(tetrapropenylsuccinimido)-oxamide--;

Column 8, line 10, "N,N'bis(phthalimido)oxamide #-#dimethyl sulfoxide" should read --N,N'-bis(phthalimido)oxamide-dimethyl sulfoxide"--;

Column 8, line 58, "5.8-8.9µ" should read --5.8-5.9µ--;

Column 10, line 10, "N'N'-bis(isophthalimido)oxamide" should read --N,N'-bis(isophthalimido)oxamide--;

Column 10, line 32, "in in" should read --in--;

Column 11, line 2, "begin" should read --begins--;

Column 12, Table III, line 16, "N,N-" should read --N,N'--;

Column 12, line 34, "N,N-bis(phthalimido)-oxamido" should read --N,N'-bis(phthalimido)oxamide--;

UNITED STATES PATENT OFFICE
CERTIFICATE OF CORRECTION

Patent No. 4,100,132      Dated July 11, 1978

Inventor(s) Harry Elwyn Hill

It is certified that error appears in the above-identified patent and that said Letters Patent are hereby corrected as shown below:

Column 12 Table IV, line 48-9 "N,N'-bis(phthalimido)oxamide" should read --N,N'-bis(phthalimido)-oxamide--;

Column 15, line 65, "N,N-bis(4-cyclohexene-1,2-dicarboximido)oxamide" should read --N,N'-bis(4-cyclohexene-1,2-dicarboximido)oxamide--;

Column 16, line 33, "presence to" should read --presence of--;

Column 16, line 46, "dehydrocylclize" should read --dehydrocyclize--.

Signed and Sealed this

Twenty-seventh Day of March 1979

[SEAL]

Attest:

RUTH C. MASON
Attesting Officer

DONALD W. BANNER
Commissioner of Patents and Trademarks